(12) United States Patent
Kaplan

(10) Patent No.: US 7,628,491 B2
(45) Date of Patent: Dec. 8, 2009

(54) ANOMALOSCOPE

(76) Inventor: George Kaplan, 2901 S. Skyline Dr., Inverness, FL (US) 34450

( * ) Notice: Subject to any disclaimer, the term of this patent is extended or adjusted under 35 U.S.C. 154(b) by 22 days.

(21) Appl. No.: 12/133,925

(22) Filed: Jun. 5, 2008

(65) Prior Publication Data
US 2009/0073385 A1     Mar. 19, 2009

Related U.S. Application Data

(60) Provisional application No. 60/973,001, filed on Sep. 17, 2007.

(51) Int. Cl.
*A61B 3/02*    (2006.01)
(52) U.S. Cl. .................. 351/242; 351/243; 351/237; 351/221
(58) Field of Classification Search ............ 351/242
See application file for complete search history.

(56) References Cited

U.S. PATENT DOCUMENTS

| | | | | |
|---|---|---|---|---|
| 4,285,580 A | * | 8/1981 | Murr ................... | 351/242 |
| 4,765,731 A | * | 8/1988 | Williams ............. | 351/243 |
| 4,798,458 A | | 1/1989 | Gehrung et al. | |
| 4,861,154 A | * | 8/1989 | Sherwin et al. ...... | 351/205 |
| 5,297,559 A | * | 3/1994 | Severns ............... | 600/558 |
| 6,220,708 B1 | * | 4/2001 | Koest .................. | 351/242 |

FOREIGN PATENT DOCUMENTS

DE    32 09 455 A1    9/1983

\* cited by examiner

*Primary Examiner*—Jessica T Stultz
(74) *Attorney, Agent, or Firm*—Martin Fleit; Paul D. Bianco; Fleit Gibbons Gutman Bongini & Bianco PL

(57) ABSTRACT

An anomaloscope for measuring and monitoring color vision, whereby gross and subtle color vision changes due to a disease process may be readily monitored over time. The device has a series of bicolor or red/green light sources presented in pairs with amber/yellow light sources, for comparison with the red/green light sources. By varying the mix of red and green light, a progression is established. A test subject indicates a perceived match between a pair consisting of a red/green light and a yellow light, to indicate the tester's sensitivity to color.

10 Claims, 5 Drawing Sheets

ANOMALOSCOPE

CROSS REFERENCE TO RELATED APPLICATION

This application claims the benefit under 35 U.S.C. 119(e) of U.S. provisional patent application No. 60/973,001, filed on Sep. 17, 2007, the contents of which is herein incorporated by reference.

FIELD OF THE INVENTION

The present invention relates to apparatus for the measuring of genetically predetermined color vision, and a method of monitoring color vision changes due to disease processes, and to an anomaloscope.

BACKGROUND OF THE INVENTION

Many apparatuses and methods have been advanced for the measurement of color vision in human subjects. Color lanterns, color threads, pseudo-isochromatic color charts and anomaloscopes.

Whereas the prior art apparatuses and methods deal with all general aspects of the problem, none offer a unique, simple, effective and portable laboratory-grade apparatus and method for routine use in a clinical setting.

As noted above, the testing of human color sense is important for diagnosis, and in particular, the testing of the color-differentiating capability of humans in the red-green range. The tests of the human color sense are today carried out mostly by pigment samples (for example, so called pseudo-isochromatic tables), with transparent color filter glasses (color test plate) or by mixing and comparing spectral lights with the anomaloscope according to Nagel. The anomaloscope of Nagel determines the capability of seeing colors in relationship to the seeing of red-green. The determination is made by comparing a binary mixture of a red and a green spectral light with a monochromatic yellow. From the mixture ratio and the adjusted luminous density of the comparison yellow, it is possible to recognize the color emmetropia of the person being tested with respect to seeing red-green. The anomaloscope according to Nagel has a mechanically very expensive construction. It also has already been suggested to use luminescence diodes for color tests, whereby two diodes of the same color are used, the brightnesses of which are modulated. From Offenlegungsschrift No. 32 09 455 it is furthermore known to use two luminescence diodes for a device of the quantitative testing of the color sense and its disorders, whereby one luminescence diode emits a yellow light and the second luminescence diode is a so called two-color luminescence diode, which emits both a red and also a green light. By mixing the red and the green, substantially monochromatic, light sources it is possible to simulate the color frequencies in the red-green range. In the practical design of such a device, the two luminous diodes are arranged relatively close to one another, such that the person being tested must judge these two luminous diodes with respect to their color characteristic and brightness. Experience has shown that the measured values obtained with such a device cannot be compared with the standardized values which are fixed in the norm.

The basic purpose of the invention is to provide a hand-held anomaloscope of the abovementioned type such that the same permits a standard testing corresponding with the anomaloscope of Nagel. In comparison to the known anomaloscope, the novel design is substantially simpler and thus less expensive to manufacture and offers the possibility of providing the person being tested a neutralizing white stimulus field between the individual measurements as suggested in U.S. Pat. No. 4,798,458.

SUMMARY OF THE INVENTION

It is an object of the invention to provide a method and apparatus that can effectively measure genetically predetermined color vision, as well as monitor, for example, for diagnostic purposes, gross and subtle color vision changes due to disease processes, such as for example cataracts, multiple sclerosis, and macular degeneration. It is a further object to provide a hand-held anomaloscope that is portable, and that may be quickly and easily used, whereby measurements may readily be made over time, and whereby a disease process may be easily monitored.

The device detects very subtle changes in color perception . . . whether genetically or pathologically acquired. It will measure the full spectrum whether genetically or pathologically acquired. It will measure the full spectrum of red/green deficits, and will measure losses in the yellow/blue frequencies. It will track changes in color vision over time to allow monitoring of conditions, i.e., muscular sclerosis, cataracts, macular degeneration. It is a diagnostic device used for the early detection of the above. It is a true anomaloscope and is pocket portable.

The subject is to select a pair of "up and down" squares of light that are closest in color match . . . i.e. One of the bottom lights (control) will closely match one of the upper lights (test). A normal match will be the first two or four lights to the patient's left. Any color matches to the right of these indicate increasing magnitudes of deficient color vision into the greens.

In accordance with an embodiment of the invention, a number of bicolor light sources, or test colors, and a corresponding number of yellow light sources, or control colors, are inserted into tubes which serve as color-mixing chambers. A diffusing screen is disposed about the ends of the tubes, covering the light emitting ends of the tubes. The bicolor light sources are disposed in an array adjacent to an array of yellow light sources, whereby output from a bicolor light source is disposed in proximity to output from a corresponding yellow light source, whereby the related outputs may be readily compared by a viewer.

In accordance with one embodiment of the invention, the light sources are LEDs, although any of a variety of light sources may be used, provided they are capable of generating the desired colors.

In accordance with a further aspect of the invention, the bicolor LEDs comprise a red and a green LED. Further, the relative strength of each of two mated bicolor LEDs may be adjusted to yield different resultant colors.

In accordance with yet another aspect of the invention, a range of colors are produced where one red/green, or bicolor tube produces a color which substantially matches output from its corresponding yellow tube, and remaining bicolor tubes have progressively more red, or progressively more green, in their respective color mixes.

In accordance with another aspect of the invention, a test subject indicates which pair of bicolor tubes most closely appears to match its corresponding yellow tube. In this manner, the subject's sensitivity to red and or green light may be evaluated.

In a further embodiment of the invention, electronic circuitry controls the relative mixture of red and green light in the bicolor tubes, and may also control the intensity of the yellow light in the yellow tubes.

In accordance with another embodiment of the invention, a printer is provided to record settings and observed results.

In an embodiment of the invention, a wireless communication interface is provided for communication between the apparatus in accordance with the invention, and the printer, a computer, or other devices.

In another embodiment of the invention, means are provided for powering and controlling the device, including a battery, one or more switches including a power switch, and means for recharging a battery powered device, or means for connecting the device to a supply of electricity.

In yet another embodiment of the invention, a method is provided for generating results quickly, for example within minutes, and wherein the device may be used to detect extremely small color vision changes, fluctuations, and variations over time, whereby a subject may be conveniently evaluated over time, or during the course of a disease process.

DETAILED DESCRIPTION OF THE INVENTION

The anomaloscope system of the invention provides a method and apparatus that can effectively measure genetically predetermined color vision, as well as monitor, for example for diagnostic purposes, gross and subtle color vision changes due to disease processes, such as for example cataracts, multiple sclerosis, and macular degeneration. The anomaloscope is portable, being packaged in a durable and lightweight container, such as may easily fit in a pocket or carrying bag. As such, and with an easy to use interface, it may be quickly and easily deployed, whereby measurements may readily be made over time, and whereby a disease process may be easily monitored.

Figure 1:
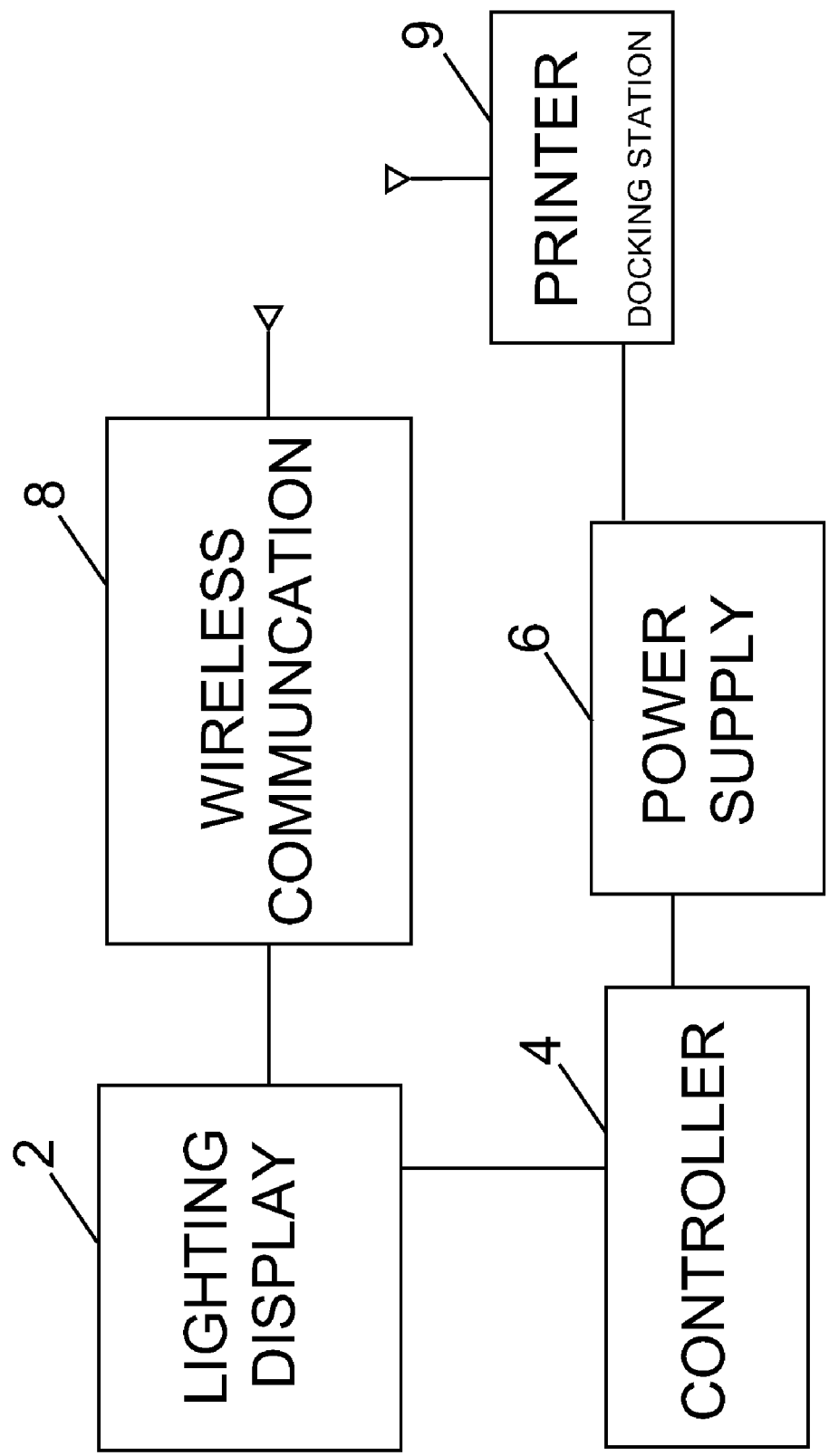
FIG. 1 shows a block diagram of the principal components of the anomaloscope system of the invention.

A block diagram is shown in FIG. 1 and consists of block 2 that contains the lighting display and circuitry, block 4 that constitutes the controller for the lighting display, block 6 a power supply, wireless communication circuitry with antenna in block 8 and block 9 containing an antenna, wireless receiving communication circuitry, a printer and docking station for receiving wirelessly the signals from block 8 and for recharging the batteries of the hand-held anomaloscope.

Figure 2:
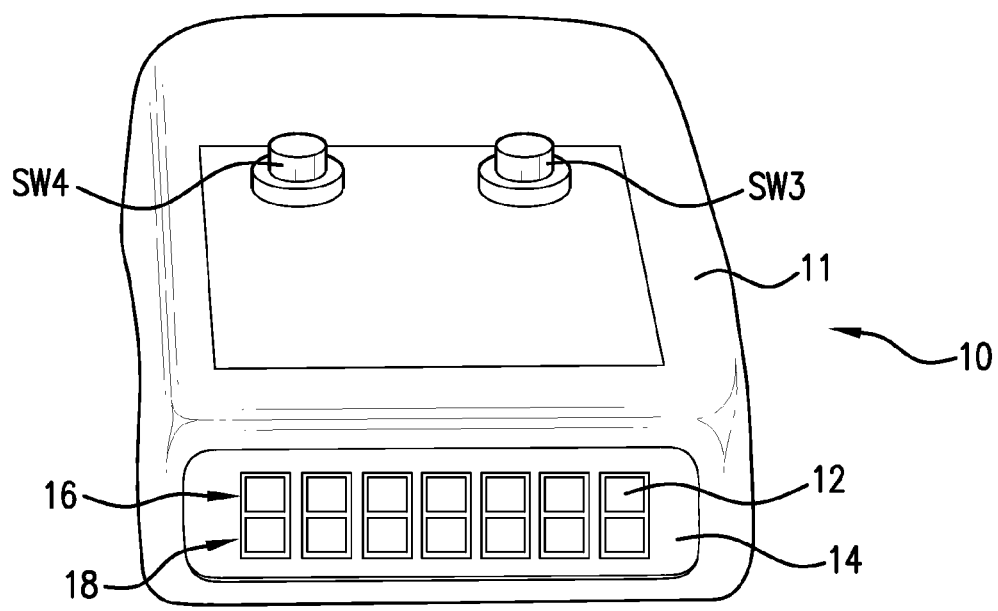
FIG. 2 shows in perspective the hand-held anomaloscope of the invention.

In accordance with a preferred embodiment of the invention, the hand-held device 10 is shown in FIG. 2 and comprises housing 11 in which is mounted a number of bicolor light sources, or test colors, and a corresponding number of yellow/amber light sources, or control colors (see schematic diagrams of FIGS. 3 and 4), inserted into tubes 12 which serve as color-mixing chambers. A diffusing screen 14 is disposed about the ends of the tubes, covering the light emitting ends of the tubes. The bicolor light sources 16 are disposed in an array adjacent to an array of yellow light sources 18, whereby output from a bicolor light source is disposed vertically in proximity to output from a corresponding yellow light source, whereby the related paired outputs may be readily compared by a viewer.

In accordance with a preferred embodiment of the invention, the light sources are LEDs, although any of a variety of light sources may be used, provided they are capable of generating the desired colors.

In accordance with a further aspect of the invention, the bicolor LEDs comprise a red and a green LED, and the relative strength of each of two mated bicolor LEDs are adjusted to yield different resultant colors.

A range of colors are produced where one red/green, or bicolor tube produces a color which substantially matches output from its corresponding yellow tube, and remaining bicolor tubes have progressively more red, or progressively more green, in their respective color mixes.

In accordance with the invention, a test subject indicates which pair of bicolor tubes most closely appears to match its corresponding yellow tube. In this manner, the subject's sensitivity to red and or green light can be evaluated.

Figure 6:
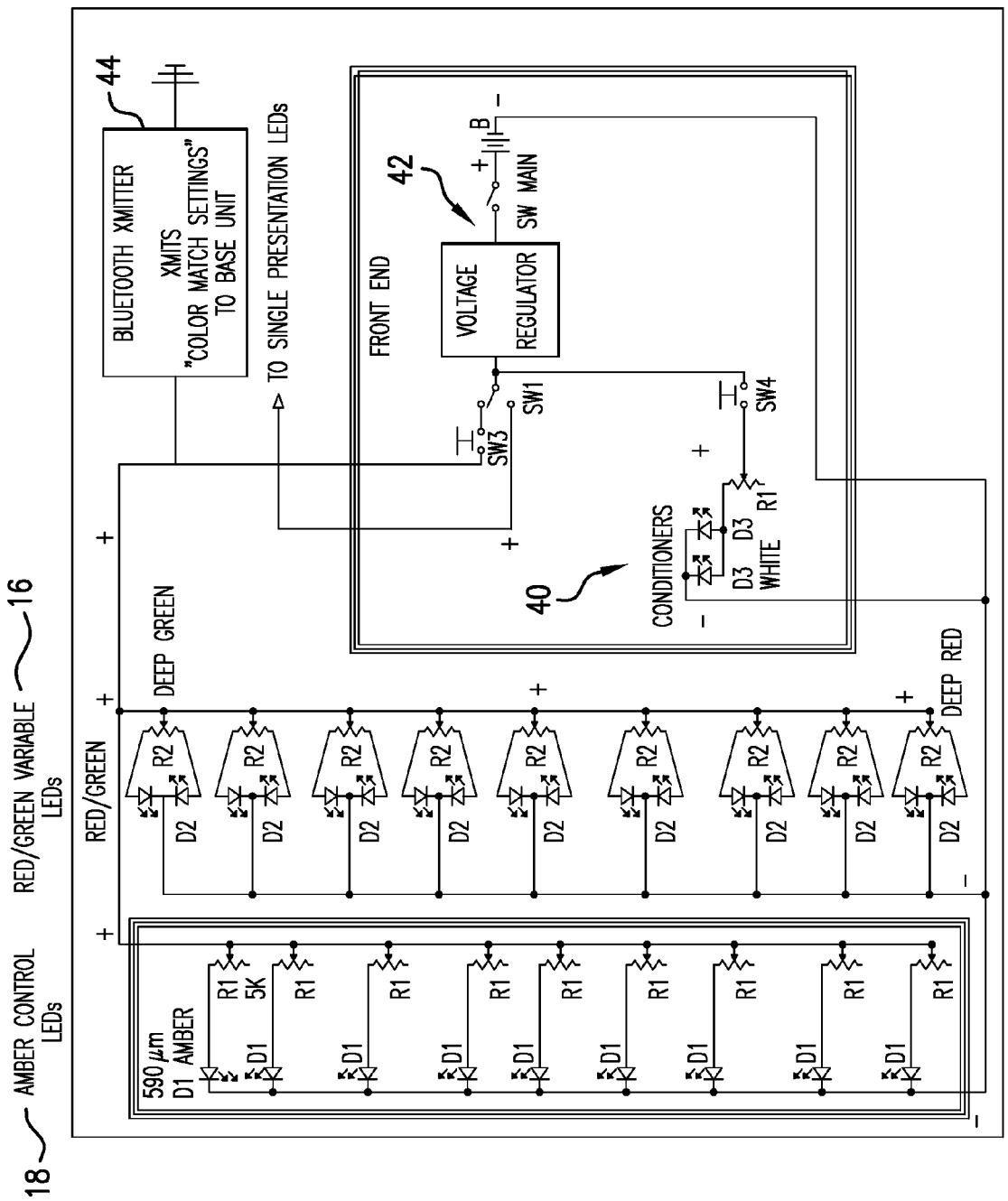
FIG. 6 is a schematic diagram of the circuitry of simultaneously presenting the LEDs to the patient.
Figure 7:
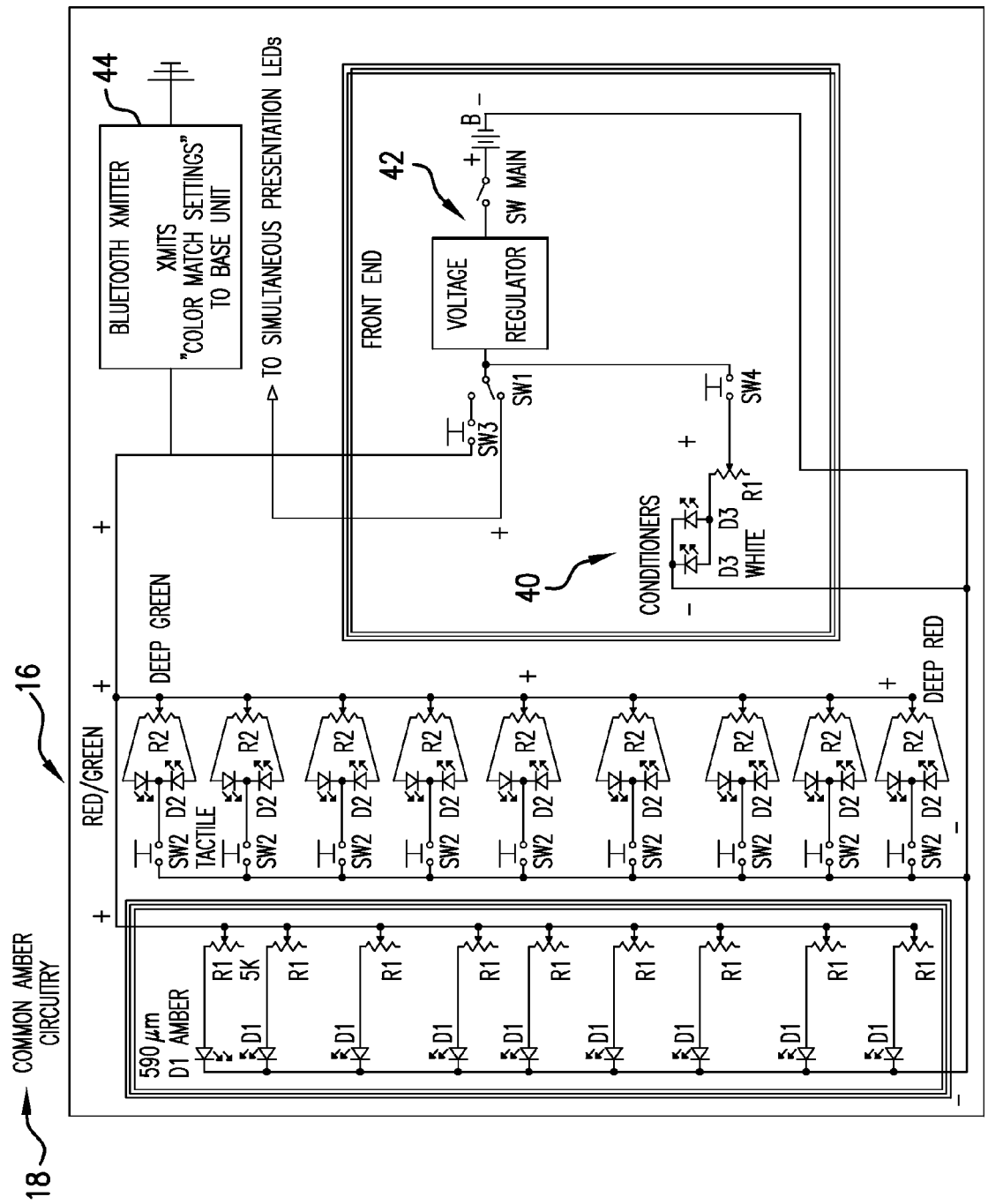
FIG. 7 is a schematic diagram of the circuitry of singularly presenting the LEDs to the patient.

The electronic circuitry of FIGS. 6 and 7 controls the relative mixture of red and green light in the bicolor tubes, and also controls the intensity of the yellow light in the yellow tubes.

A printer, see block 9, FIG. 1, is provided to record settings and observed results.

A wireless communication interface, see block 8, FIG. 1, is provided for communication between the apparatus in accordance with the invention, and the printer, a computer, or other devices. The base unit will also serve as a docking station/battery charger for the handhelds.

Power means are provided for powering and controlling the device, including a battery, one or more switches including a power switch, and means for recharging a battery powered device, or means for connecting the device to a supply of electricity.

The method provides for generating results quickly, for example within minutes, and wherein the device may be used to detect extremely small color vision changes, fluctuations, and variations over time, whereby a subject may be conveniently evaluated over time, or during the course of a disease process.

As can be seen in FIG. 1, the hand-held device in accordance with the invention has two switches SW3 and SW4 are located on top of the housing, a viewing screen on one end of the housing shows the lighting tubes, and a battery compartment is provided in the housing. In this embodiment, the dimensions are approximately 3"×1.5"×6". It is expected that a high volume manufactured embodiment may be considerably smaller. As shown, seven (7) pairs of lights are provided, but the number can be increase to up to fourteen pairs. The bottom row of seven lights are amber colored, having a wavelength of approximately 589 nm. The upper row of seven lights varies in color in a progressive order from red, on the left, to a green, on the right (the tests). The object is to indicate which pair of lights matches the closest in color. The device is organized so that the closest match, normally, are the leftmost upper and lower pair, while any selections to the right indicate increasing relative amounts of color vision anomaly. In this case, selections to the right of normal indicate a "green weak" condition of deuteranomally. Red weakness, or protanomally, can be measured when the upper row of colors are skewed progressively from amber into the red end of the spectrum.

The device is organized so that when switch SW3 button is depressed, all pairs of lights are illuminated. The patient then selects the pair that "matches". Alternatively, according to FIGS. 6 and 7, the lights can be turned on all at once or singularly in pairs.

A combination of two buttons (switches) may be pressed, or the buttons may be pressed in sequence, to activate specific light pairs. Alternatively, additional buttons may be provided. In this manner, a tester may illuminate pairs of tubes individually, or in groups, to refine or modify the testing process. Test pairs including a pure red light, and a pure green light, to measure for extreme color anomalies are additionally contemplated, activated by switches, or provided as dedicated pairs.

When switch SW4 button is depressed, white light sources, such as LEDs, are projected onto the viewing screen. This is known as the "conditioning" light, and is necessary because if one stares at colors too long, the color sensitive cones on the retina of the eye will become "bleached out", or desensitized, and the test becomes unreliable. The tester will intermittently illuminate these LEDs to "reset" the sensitivity of the cones.

A battery compartment of conventional design is contained within the housing in a known manner.

Figure 3:
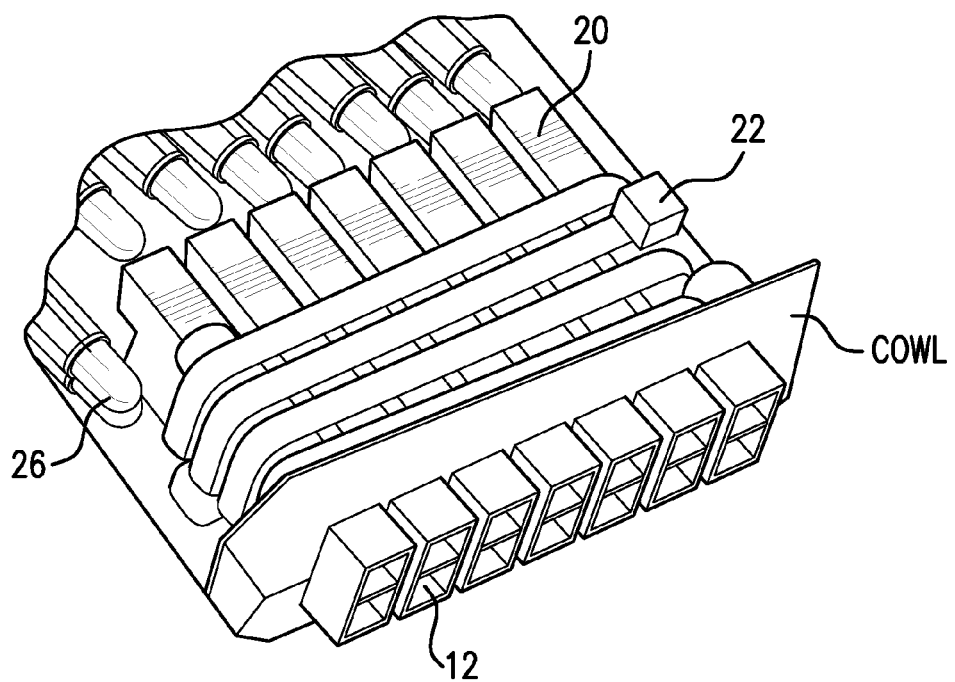
FIG. 3 shows in a perspective view the details of the light tubes with the LEDs inserted.
Figure 4:
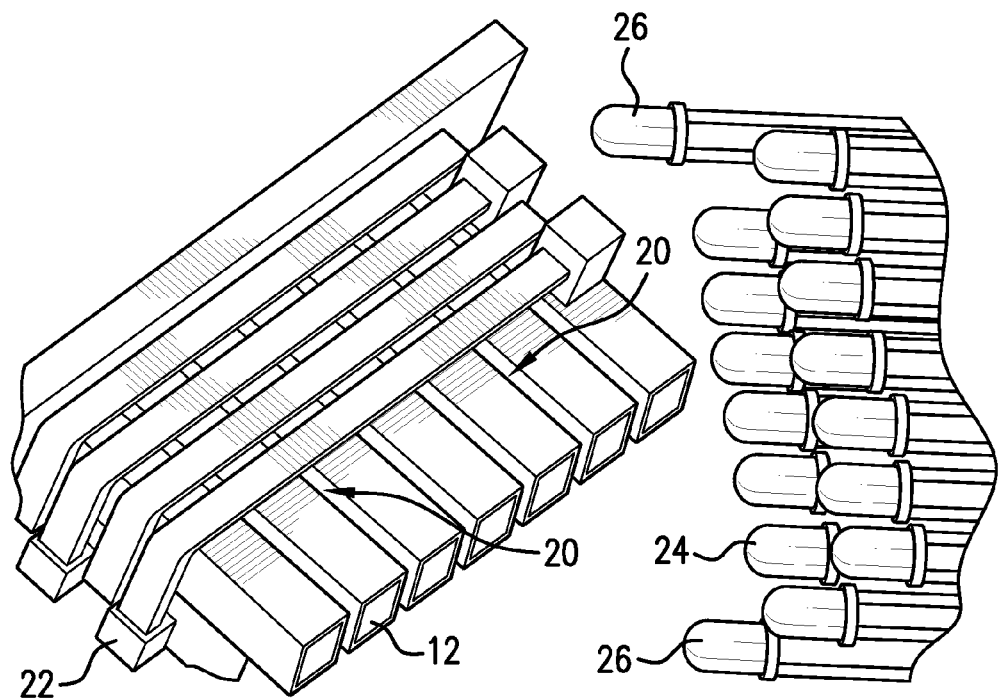
FIG. 4 shows in an exploded view the details of the light tubes and the LEDs to be inserted.
Figure 5:
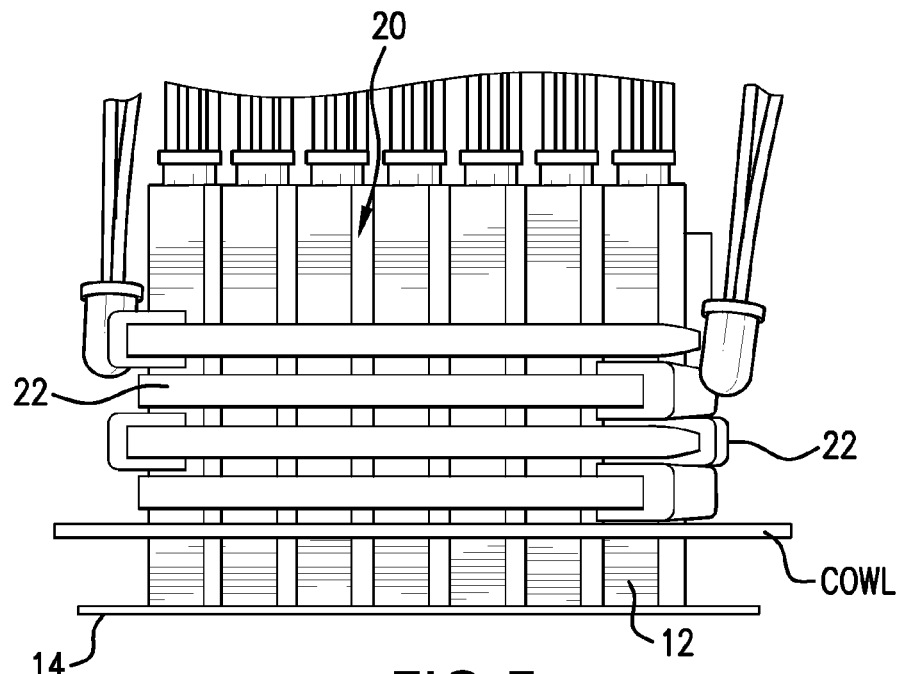
FIG. 5 is a plan view of the light tubes with LEDs inserted.

With reference to FIGS. 3-5, the interior of the housing is shown with respect to the light tubes 12 and the LEDs 24.

The elongated rectangular tubes 12 are mounted in the two-high vertical array using spacers 20 and nylon guides 22, and provide a series of paired color-mixing chambers. Two rows of LEDs 24 are inserted into the rear ends of the tubes 12, as can be readily seen in the views of FIGS. 3-5. The translucent viewing screen 14 is a panel covering the front ends of the tubes 12. The white conditioning, stand-alone LEDs 26 are located on both side of the color LEDs 24 and tubes 12 arrays.

With reference to FIGS. 3-5, spacers 20 are visible between corresponding pairs of bicolor and amber mixing tubes 12. This serves as a guide, or indicator to the test subject, of the requirement to compare the colors of upper and lower tubes 12 paired vertically by proximity, and not between horizontally spaced apart adjacent tubes 12. A translucent cowl fabricated from nylon, may be seen in FIGS. 3-5, disposed about the front end of the tubes 12. The cowl serves to maintain the tubes in alignment, and additionally serves as a diffuser for the conditioning lights disposed at each side of the "test" and "standard" arrays.

The translucent viewing screen 14 lies against the tubes 12 at their ends, as may be seen in the Figures. The viewing screen serves to diffuse light emerging from the tubes, as well as to diffuse the conditioning light.

The five subsystems comprising the anomaloscope system in accordance with the invention are a number of red/green (bicolor) LEDs and a corresponding number of yellow LEDs (in this embodiment, seven LEDs of each color, fourteen LEDs in all). Each separate LED is inserted into one end of its own separate hollow "optical" tube, all of equal length, which serves as a color-mixing chamber. Covering the other end of each tube 12 is the white translucent view-screen 14 onto which the LED colors are projected, through the tube and onto the screen, through which the colors can be seen. The red/green tubes are arrayed side-by-side, in a horizontal row, such that the tubes are similarly oriented, with ends facing in the same direction and being flush with each other. An on-end view of this arrangement would yield a 1×7 array of view-screens. The yellow tubes are similarly aligned forming a second 1×7 array of view-screens. The two separate horizontal arrays of LEDs (red/green and yellow) are juxtaposed vertically, one above the other, such that each red/green view-screen is paired with a corresponding yellow view-screen. An on-end view of this arrangement yields a 2×7 array of view-screens, red/green on top, yellow on bottom, see FIG. 2. The red/green view-screens serve as the test colors and the yellow view-screens serve as the control (standard) colors. In each red/green tube (bicolor LED) the red and green colors are mixed in varying proportions so as to yield different colors along the red/green color chromaticity axis, from 100% pure red through 100% pure green, including yellows in the middle ranges. The red/green color mixtures are calibrated in a manner where only one red/green tube color-matches the standard yellow color from its corresponding yellow tube, and the balance of the red/green tubes are calibrated to colors that are slightly skewed into the green and red side of the color-matching tubes in progressive steps. Color vision status is measured by the subject simply indicating which pair of view-screens (red/green tube & yellow tube) appears to match most closely as to color and brightness. This matching-pair is then compared to the "normalized" match pair which indicates normal color vision, or degrees of red blindness, and green blindness, respectively.

Subsystem two comprises the electronic circuitry, as described above, that controls the red/green LED color mixtures and intensities, and the intensities of the yellow standards.

Subsystem three comprises a portable printing unit, such as a thermal printer.

Subsystem four comprises wireless communication electronics, such as bluetooth, for unit to unit communication, as between the testing apparatus and the printer, or the testing apparatus and a computer.

Subsystem five comprises the battery or plug in power source, and switches for control, including an on-off switch mechanism, and user control switches, as described above.

Another object of the present invention is to provide an apparatus and method for the measuring of genetically predetermined color vision, and a method of monitoring color vision changes due to disease processes. The device and method described herein provides for substantially instantaneous test results; is sensitive to extreme small color vision changes, fluctuations and variations; is substantially unaffected by ambient lighting; is small/pocket-portable; has laboratory grade accuracy; is simple to administer and understand; and is appropriate and easily modifiable for a wide variety of uses, including but not limited to neurological testing, pediatrics, cataract demonstrations, macular degeneration progression, industrial screening, and in-school screenings. Modifications to optimize the device for each environment are contemplated in accordance with the invention.

By communicating with a printer, or a storage medium, possibly associated with a personal computer, the tester can save or print the results, to establish a record, and to facilitate comparisons and evaluation of changes over time.

Each color mix or standard color tube forms a type of anomaloscope, wherein the tubes are assembled together and may be shown to the patient simultaneously. Used in this manner, the device functions as a screening device that immediately flags a likely color problem. The patient picks the best color match, which describes the state of color perception.

A device in accordance with the invention conveniently and inexpensively serves as a tool in each exam room in a clinic or doctor's office, or it may be carried in the physician's or health practitioner's pocket. One or more docking stations may be provided, where the portable devices may be placed for charging, data download, and storage.

It is further contemplated that a variety of electronic components, in addition to the ones described more fully herein, may be used as is known in the relevant arts, including potentiometers, resistors, voltage regulators, and digital readouts.

A larger device in accordance with the invention is also contemplated, capable of a wider array of color gradations for more precise measurements for tracking small changes. Said device may include continuously adjustable solid state anomaloscope color tube units as described herein, that will be substantially infinitely adjustable for exact measurements of color perception. A device such as is described may be more suitable for precise laboratory measurements.

FIGS. 6 and 7 show schematically the circuitry for the LEDs 24 and their control. The circuitry includes the conditioning circuitry 40 for the conditioning LEDs 26, voltage regulation 42, Bluetooth transmitter 44 for sending out color match settings, the red/green variable LEDs 24, and the amber control LEDs 24. Switches are provided, as shown in the schematic so that FIG. 6 shows the schematic for simultaneous presentation of all the LEDs 24, whereas, FIG. 7 shows the schematic for single presentation of the LEDs 24 in pairs.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. An anomaloscope comprising a housing, a pair of arrays of horizontally disposed elongated light tubes each having a front end and a rear end, spacers between adjacent tubes to maintain them is spaced relation, guides holding the tubes in parallel one to the other with the tubes of one array being positioned in vertical alignment with the tubes of the other array so that the tubes are paired vertically with one tube of each vertical pair positioned above its associated paired tube, a translucent viewing screen positioned at the front ends of the tubes, an LED inserted into each tube, power circuitry to power the LEDs, control circuitry to control the illumination of the LEDs so that all LEDs can be lighted one of simultaneously and singularly paired, the LEDs inserted into one of the horizontal arrays producing an amber light, the LEDs inserted into the other of the horizontal arrays producing light from a bicolor light source with the color varying from one end of the other array to the other end of the other array.

2. An anomaloscope according to claim 1 wherein the control circuitry can selectively control the illumination of the LEDs so that all LEDs can be selectively lighted simultaneously or singularly paired.

3. An anomaloscope according to claim 1 wherein the bicolor light source is red/green.

4. An anomaloscope according to claim 1 wherein the bicolor light source is blue/yellow.

5. An anomaloscope according to claim 1 further including wireless communicating circuitry and an antenna for wirelessly transmitting to a remote device.

6. An anomaloscope according to claim 1 further including conditioning lights, a controller therefore, and manual switch means for actuating the controller.

7. An anomaloscope according to claim 6 wherein the conditioning lights produce a white light.

8. An anomaloscope according to claim 1 further including a cowl surrounding the front ends of the tubes between the guides and the translucent screen.

9. An anomaloscope according to claim 8 wherein the cowl is composed of a material that is translucent.

10. An anomaloscope according to claim 7 further including a cowl surrounding the front ends of the tubes between the guides and the translucent screen with the conditioning lights being positioned to the rear of the cowl, said cowl being composed of a material that is translucent whereby the conditioning lights will be diffused.

* * * * *